(12) United States Patent
Cech

(10) Patent No.: US 6,894,775 B1
(45) Date of Patent: May 17, 2005

(54) SYSTEM AND METHOD FOR INSPECTING THE STRUCTURAL INTEGRITY OF VISIBLY CLEAR OBJECTS

(75) Inventor: Steven D. Cech, Aurora, OH (US)

(73) Assignee: Pressco Technology Inc., Cleveland, OH (US)

( * ) Notice: Subject to any disclaimer, the term of this patent is extended or adjusted under 35 U.S.C. 154(b) by 0 days.

(21) Appl. No.: 09/980,851

(22) PCT Filed: Apr. 27, 2000

(86) PCT No.: PCT/US00/11308

§ 371 (c)(1),
(2), (4) Date: Jun. 11, 2002

(87) PCT Pub. No.: WO00/66283

PCT Pub. Date: Nov. 9, 2000

Related U.S. Application Data

(60) Provisional application No. 60/131,561, filed on Apr. 29, 1999.

(51) Int. Cl.[7] .............................................. G01N 21/00
(52) U.S. Cl. ................... 356/239.1; 356/239.4
(58) Field of Search .................. 356/237.1–237.5, 356/239.1–239.8, 240.1; 250/372, 223 B

(56) References Cited

U.S. PATENT DOCUMENTS

| | | | |
|---|---|---|---|
| 3,356,203 A | | 12/1967 | Noble et al. |
| 3,721,501 A | * | 3/1973 | Atkinson et al. ........... 356/432 |
| 3,778,617 A | | 12/1973 | Calhoun |
| 4,121,103 A | * | 10/1978 | Calhoun ..................... 250/343 |
| 4,367,405 A | | 1/1983 | Ford |
| 4,486,776 A | | 12/1984 | Yoshida |
| 5,073,708 A | * | 12/1991 | Matsumoto et al. ..... 250/223 B |
| 5,095,204 A | * | 3/1992 | Novini ................... 250/223 B |
| 5,141,110 A | | 8/1992 | Trischan et al. |
| 5,443,164 A | * | 8/1995 | Walsh et al. ................. 209/580 |
| 5,502,559 A | * | 3/1996 | Powell et al. .................. 356/73 |
| 5,583,337 A | | 12/1996 | Chan |
| 5,917,602 A | * | 6/1999 | Bonewitz et al. ........... 356/614 |
| 6,049,379 A | * | 4/2000 | Lucas ....................... 356/240.1 |
| 6,089,108 A | * | 7/2000 | Lucas ......................... 73/865.8 |
| 6,188,079 B1 | * | 2/2001 | Juvinall et al. ......... 250/559.27 |

FOREIGN PATENT DOCUMENTS

| | | |
|---|---|---|
| DE | 32 45 908 A1 | 6/1984 |
| DE | 36 11 536 A1 | 10/1987 |
| EP | 0 587 037 A2 | 3/1994 |

\* cited by examiner

*Primary Examiner*—Michael P. Stafira
(74) *Attorney, Agent, or Firm*—Fay, Sharpe, Fagan, Minnich & McKee, LLP

(57) ABSTRACT

An inspection system is provided comprising at least one detection element (60) sensitive to electromagnetic radiation (20) at a wavelength wherein the object (10) to be inspected is rendered opaque by naturally occurring material molecular absorptions. As such, material defects such as cracks and voids can be detected.

34 Claims, 3 Drawing Sheets

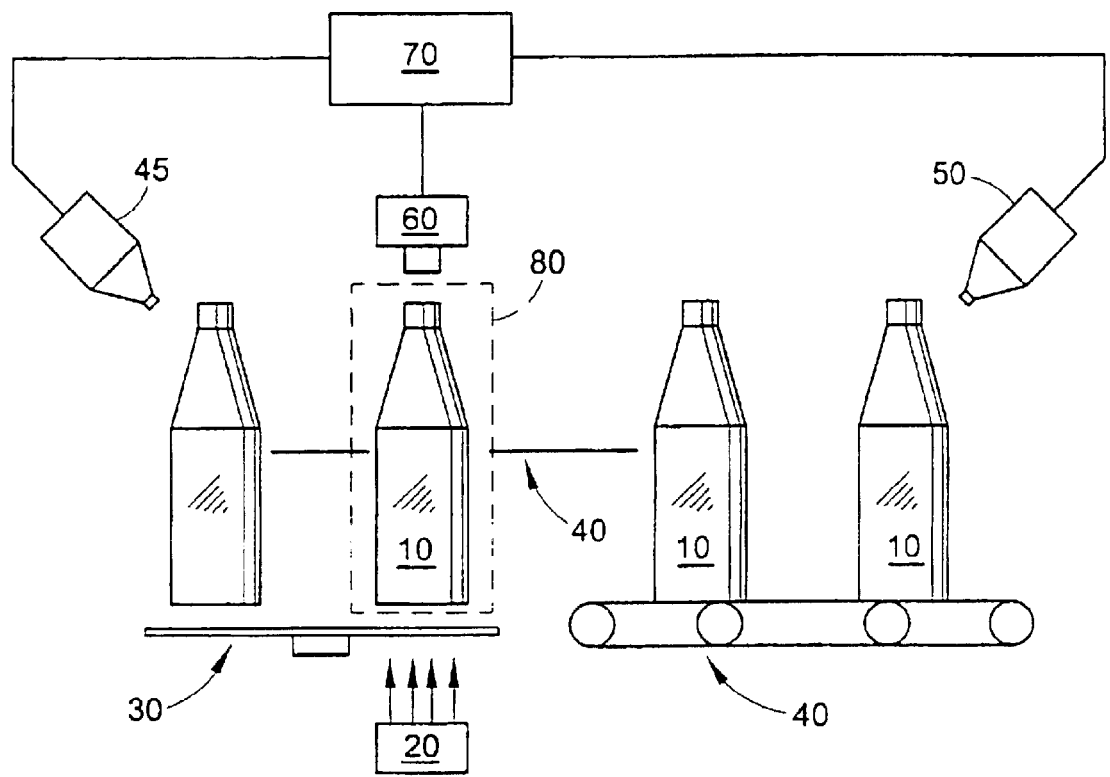
FIG. 1(a)
FIG. 1(b)
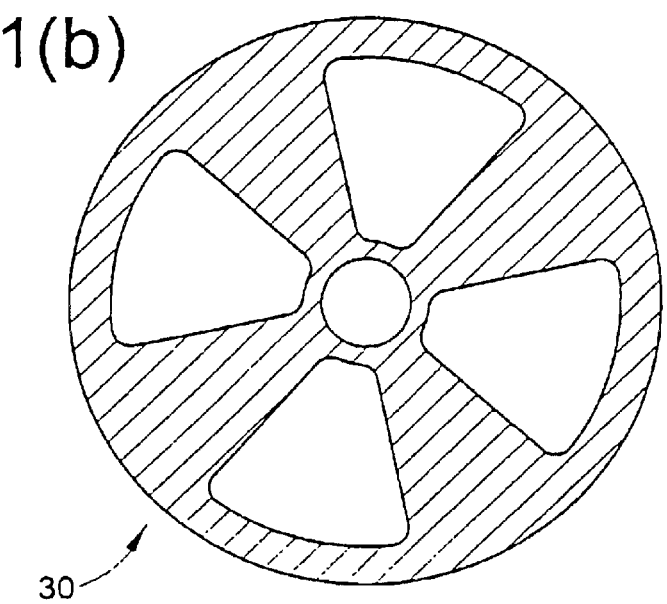

SYSTEM AND METHOD FOR INSPECTING THE STRUCTURAL INTEGRITY OF VISIBLY CLEAR OBJECTS

This application is a 371 of PCT/US00/11308 Apr. 27, 2000 which claims benefit of 60/131/561 Apr. 29, 1999.

FIELD OF THE INVENTION

This application pertains to the art of inspecting the structural integrity of visibly clear objects. In particular, it relates to the inspection of visibly clear food and/or beverage containers manufactured out of glass or plastic. Though the invention will be described with reference to those items, it should be understood that the invention has a broader application to the inspection of any manufactured or naturally occurring object having a predominately visibly-clear to structure.

BACKGROUND OF THE INVENTION

Machine vision systems providing some degree of functionality related to inspecting the structure integrity of visibly clear glass and/or plastic containers have been conceived and constructed. Generally, such systems are based on the operation of an area array sensor, most typically a CCD sensor, sensitive to energy in the visible portion of the electromagnetic spectrum (400 nm to 700 nm). For purposes of this disclosure, the term visibly clear specifically means that the material allows very high optical transmission of electromagnetic radiation (light) falling within the 400 nm to 700 nm visible wavelength range.

One fairly obvious but important fact associated with objects manufactured from visibly clear material is that it is difficult, using state-of-the-art machine vision techniques, to inspect such objects for the presence of material voids in their final formed structure. This is significant because material voids such as holes or cracks are critical part defects which compromise the intended function of the product.

Machine vision, inspection systems typically operate by measuring the spatial variations of visible light as it reflects off or transmits through the structure. Since the objects which are to be inspected by such state-of-the-art systems are predominately clear in nature, the spatial light intensity variations which result from the presence of material voids in the material structure are quite small and result in less than adequate overall system performance. Stated in other words, holes and cracks in visibly clear objects are hard to see using machine vision systems operating within the visible region of the electromagnetic spectrum.

Another attribute of current state-of-the-art inspection systems is that they require a great deal of special purpose hardware and software in order to provide any level of product inspection. Light sources, imaging optics, cameras, control electronics, and an image processing computer executing custom inspection algorithms are required for baseline system functionality. This collection of hardware and software components result in an expensive inspection solution which, in many structural inspection applications, falls short of desired performance requirements.

The subject invention overcomes the problems of limited inspection performance and high cost by providing a sensor system operating at infrared wavelengths wherein the object under inspection is naturally opaque.

SUMMARY OF THE INVENTION

In accordance with one aspect of the present invention, there is provided an inspection system comprising at least one detection element sensitive to electromagnetic radiation at a wavelength wherein the object to be inspected is rendered opaque by naturally occurring material molecular (and/or atomic) absorptions. In the disclosed invention, the discrete detection element or detector is positioned at an advantageous location wherein a transport mechanism (either a transport mechanism naturally associated with the manufacturing process or one specifically designed for the purpose of presenting the object to the inspection station) moves the object to be inspected into close proximity to the detection element to accommodate structural inspection. When the object is positioned for inspection, a source of infrared radiation containing a significant component of its emitted energy at wavelengths wherein visibly clear objects become generally opaque is disposed opposite of the detector. Properly positioned, the transported object under inspection passes through the detector/IR source line of sight. So positioned, the detector/IR radiation source components comprise a simple system capable of robustly detecting material voids occurring in the objects under inspection.

In accordance with a more limited aspect of the disclosed invention, the infrared radiation source is chopped (e.g. mechanically or electrically) at a known time-based frequency to aid in the detection of the transmitted IR signal.

Further scope of the applicability of the present invention will become apparent from the detailed description provided below. It should be understood, however, that the detailed description and specific examples, while indicating preferred embodiments of the invention, are given by way of illustration only, since various changes and modifications within the spirit and scope of the invention will become apparent to those skilled in the art.

BRIEF DESCRIPTION OF THE DRAWINGS

The present invention exists in the construction, arrangement and combinations of the various parts of the device and/or the steps of the method whereby the objects contemplated are attained as hereinafter more fully set forth in the detailed description and illustrated in the accompanying drawings in which:

FIGS. 1(a) and (b) illustrate a system according to the present invention;

DESCRIPTION OF THE PREFERRED EMBODIMENT

Figure 2:
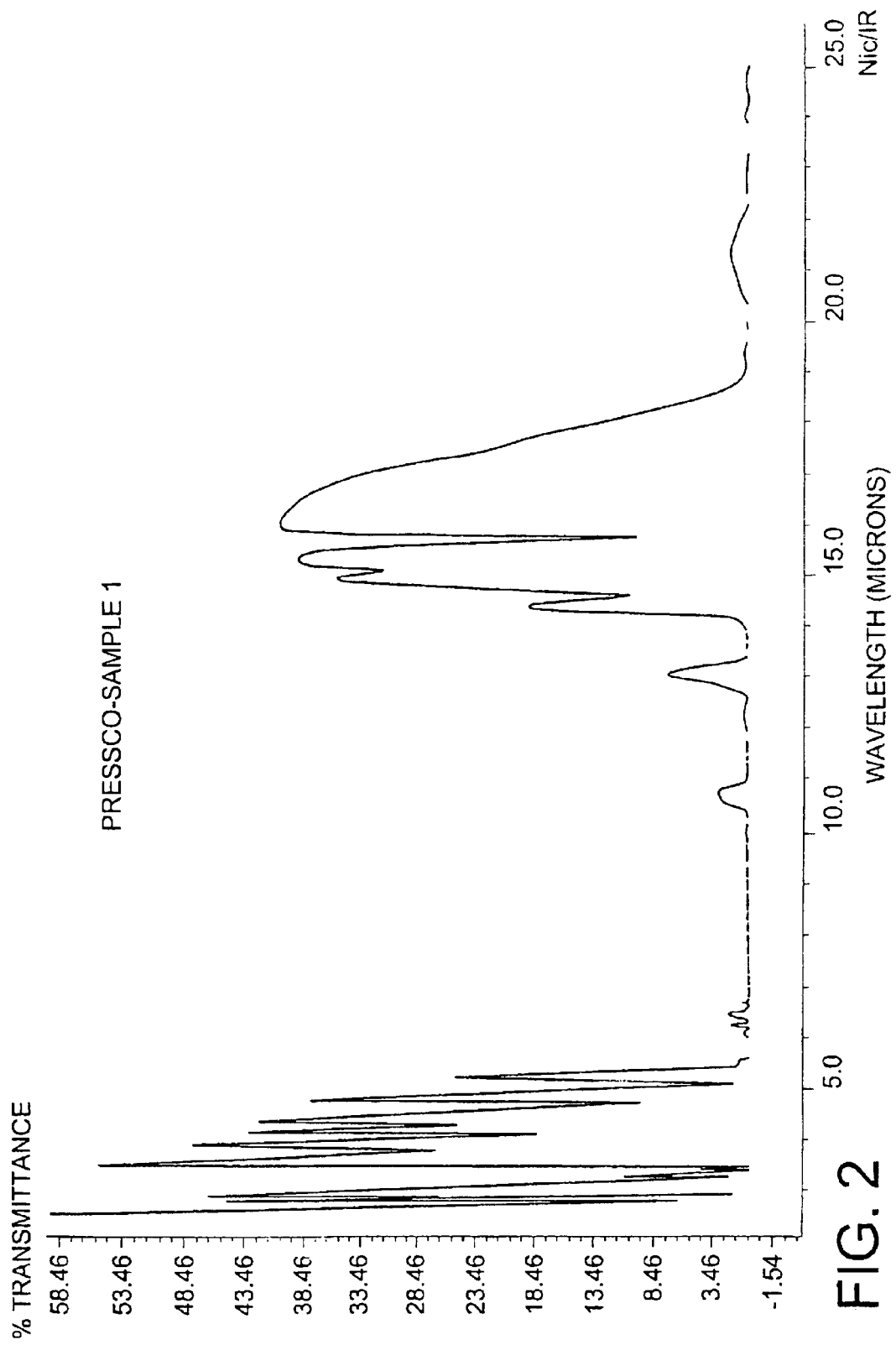
FIG. 2 shows the transmission spectrum for a sample of PET material.

One parameter often used to both qualitatively and quantitatively describe various materials is an optical attribute referred to as an optical transmission property. In laymen's terms, this parameter describes the ability of a material to allow visible light (that limited portion of the electromagnetic spectrum between 400 nm and 700 nm) to transmit therethrough. Materials which exhibit no tendency to absorb light in the visible wavelength range are defined as visibly clear materials. Glass, PET, and PEN are examples of visibly clear materials.

The above-referenced material parameter, or property, called optical transmission can be more broadly defined as the reaction of the material to electromagnetic radiation in a wavelength range extending beyond the visible spectrum. For many reasons, it is more useful to consider the wavelength range extending from 400 nm in the visible region out to 15 um in the infrared region in the qualitative definition of the optical transmission characteristics of the material. In this regard, the techniques of geometric optics apply equally well to this broader wavelength region. In addition, there are radiation sources, detectors, and optical materials and coatings commercially available for use in this broader wavelength region making it feasible to theorize and construct optical instrumentation to sense and quantify optical radiation in this broader wavelength region. When characterized over this broader range, most materials which are highly transmissive in the visible wavelength range exhibit large regions of low and even zero transmission of electromagnetic radiation in other portions of the electromagnetic spectrum.

In much of the electromagnetic spectrum, the visibly clear materials used in the construction of food and beverage containers are completely opaque to incident radiation. The subject invention takes advantage of this material phenomenon under the pretext that it will be advantageous to look for the presence of holes, cracks, or other material voids in a wavelength region wherein the material is opaque as opposed to performing the same inspection operation at wavelengths wherein the material itself is predominately clear, as is done in current inspection systems.

Referring now to the drawings wherein the figures are for the purpose of illustrating the preferred embodiments of the invention only, and not for the purpose of limiting the same. FIG. 1(a) represents an overall view of an inspection system according to the present invention. As shown, a transport mechanism 40 is utilized to position visibly clear plastic or glass articles 10 within an inspection zone 80. The transport mechanism may be a conveyor or any other suitable device or arrangement to facilitate the inspection of an object in the zone. In addition, as should be apparent to those skilled in the art, sufficient support structure, including the transport or conveyor mechanism, is provided to the system to support the source and sensor device as well as maintain the object under inspection in proper position for inspection.

In the position shown in zone 80, the object 10 under inspection is positioned within the line of sight between a detector 60 and an infrared source 20. So positioned, a specific portion of the object is subject to inspection for the presence of material voids. In the case of the preferred embodiment, the base portion of the visibly clear container can be inspected for cracks or holes using the disclosed invention. Of course, it is to be appreciated that other portions of the objects may be inspected. Moreover, it is contemplated that objects other than containers can also be inspected.

More particularly, when in the inspection zone 80, the object under inspection 10 is positioned in the line of sight between the radiation source 20 and the detector 60. The radiation source is chosen based on its ability to emit significant energy at optical wavelengths wherein the object under inspection 10 is generally opaque. For many visibly clear materials including glass, PET, and PEN, the wavelength region above 3 um contains many broad hydrocarbon-based absorption bands which severely limit optical transmission. This behavior is depicted in FIG. 2—which shows the transmission spectrum of PET from 2 um out to 25 um. The visible spectrum, not shown, corresponds to 0.4–0.7 um (or 400–700 nm). The large regions where the transmission dips to 0% indicates regions where the material is opaque. The preferred source of IR radiation at these longer wavelengths is a black body or gray body thermal radiator operating at temperatures up to about 1000° C. In addition to black body radiation sources, there exist commercially available solid-state emitters (e.g. LEDs), which may be arranged in arrays, operating at wavelengths of approximately 3 um and above which would be applicable to the subject invention. It will be appreciated that the selection of an infrared source will depend largely on the desired wavelength of operation.

Referring back now to FIG. 1, to detect and respond to the emitted infrared radiation produced by source 20, a detector 60 needs to be chosen which has a high sensitivity to incident radiation above 3 um. There are many potentially suitable single or plural element detector types which could be utilized in the subject invention including Mercury Cadmium Telluride (MCT), Lead Sulfide (PbS), Indium Antimonide (InSb), and Lead Selenide (PbSe). In more general terms, these specific detector types can be described as either photoconductive, photovoltaic, or thermal detector types. Further, it should be appreciated that the detector 60 may also be a suitable camera or any other sensor device that may comprise a one or two dimensional array of photosensitive elements.

To improve the ability of the system to detect small material voids, a chopping mechanism 30 is applied to the energy emitted by the radiation source 20 prior to interacting with the object 10 under test. Such mechanisms are well known in the thermal infrared imaging field. This concept is also similar to the one used to encode and decode AM radio transmissions.

In the preferred embodiment, the system chopper 30 is a mechanical chopper that takes the exemplary form of a rotating disk with alternating opaque/transparent regions which act to modulate the energy emitted by the radiation source 20, as is well known and illustrated in FIG. 1(b). In this fashion, the signal of interest is isolated to a specific time-based frequency (the chopping frequency) which facilitates the measurement of low level signals incident on the detector 60.

Alternatively, an electronic, or electrical, chopper may be used. For example, a pulsed infrared source (e.g. pulsed LEDs) may be used wherein the pulsing corresponds to the physical modulating of energy by the application of pulsed drive current.

In either the mechanical chopper or electronic chopper, the advantage of use is that the detector is able to better detect the signal of interest. In this regard, the signal to noise ratio of subsequently received signals is increased. In the preferred embodiment, the signal of interest corresponds to the energy that passes through a crack or void in the bottom of a container 10.

Completing the preferred embodiment of the subject invention are a control electronics module 70 and a part reject mechanism 50. These mechanisms and associated systems are well known in the inspection art. Briefly, however, the control electronics module (or processor comprising various hardware and software configurations) 70 provides power and detector bias signals to the detector 60. In return, it receives inspection information related to the objects structural integrity from the detector 60. From this output, the module 70 is able to determine a state, quality, or acceptability of objects under inspection. It then selectively uses this information to operate a reject mechanism 50 in a pass/fail mode. The reject mechanism may act to physically reject or otherwise mark for subsequent action objects determined to be out of, or alternatively, within specifications as previously standardized and encoded within the processor module 70. Moreover, in systems whereby the objects being inspected are formed in mold cavities within the system, part rejection information will also be useful to correlate and feedback to the molding components to possibly effect adjustments and corrections. Furthermore, it should be recognized that well-known, conventional machine vision and/or inspection systems typically have incorporated therein part detection devices (such as element 45 in FIG. 1), tracking features and conveyance mechanisms and systems (such as transport mechanism 40) that are deployed to interact with the objects under inspection and used to maneuver the objects under inspection into an advantageous position between the sensor and the source as well as provide instrument control signals to both the sensor and the source.

Figure 3:
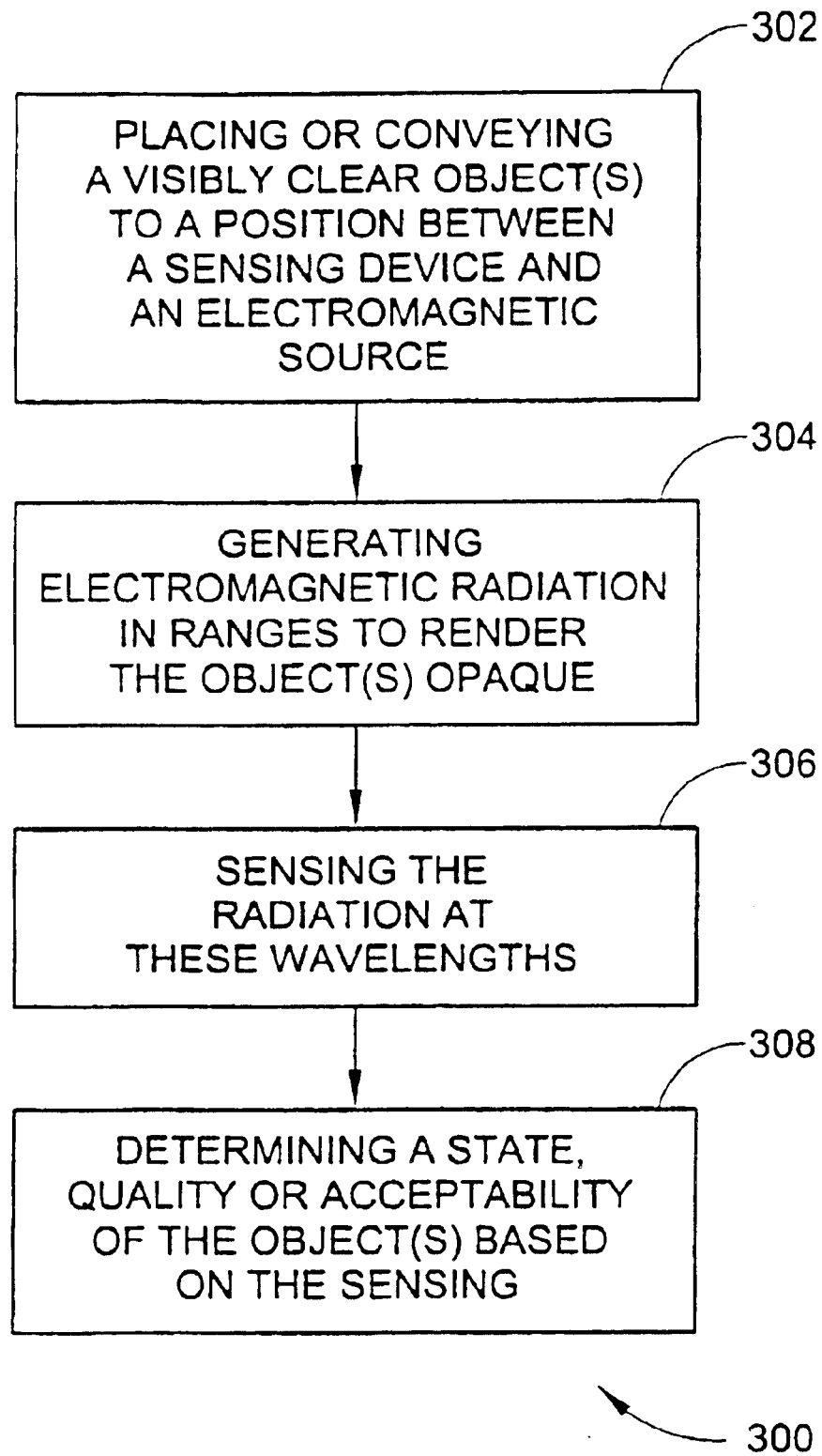
FIG. 3 is a flowchart according to the present invention.

It should be readily apparent from the detailed description above, that in operation, the system of the present invention accomplishes the method of FIG. 3 as follows. First, a visibly clear object is placed or conveyed to a position between a sensing device and an electromagnetic source (step 302). Next, electromagnetic radiation is generated by the source in wavelength ranges to render the objects under inspection opaque (step 304). The radiation is then sensed at these wavelengths, which correspond to the opaque wavelength regions of the objects under inspection (step 306). A state, quality or acceptability is then determined based on the sensing (step 308). In addition, other features of the invention as described above may be embodied in this method. For example, the generating step may include pulsing the source means to increase a signal to noise ratio of a subsequentially received electromagnetic signal.

This invention has been described with reference to the preferred embodiment. Obvious modifications and alterations will occur to others upon reading and understanding the specifications. It is intended that all such modifications and alterations be included insofar as they come within the scope of the appended claims or equivalents thereof.

Having just described the invention, I claim:

1. A sensing apparatus useful for inspecting the structural integrity of visibly clear objects, the apparatus comprising:
   a sensor device operative to respond to electromagnetic radiation at one or more wavelengths or wavelength ranges corresponding to electromagnetic energy transmission wherein the objects are rendered opaque by naturally occurring molecular and/or atomic absorptions occurring within material comprising the objects;
   an electromagnetic radiation source wherein a significant portion of an emitted spectrum therefrom occurs in the ranges wherein the objects are generally opaque; and,
   a support structure positioned to support the sensor device and source and to maintain the objects in between the source and the sensor device.

2. The apparatus of claim 1 wherein the sensor device is comprised of a single-element photoconductive, photovoltaic, or thermal detector.

3. The apparatus of claim 2 further comprising a processor operative to receive an output of the sensor device and operate on the output to determine the state, quality, or acceptability of the objects.

4. The apparatus of claim 3 further comprising part detection, tracking, and conveyance systems deployed to interact with the objects and used to both maneuver the object under test into an advantageous position between the sensor element and the source and to provide instrument control signals to both the sensor device and the source.

5. The apparatus of claim 4 further comprising a reject system which receives the processed output of the processor and acts to physically reject or otherwise mark for subsequent action objects.

6. The apparatus of claim 5 wherein the source comprises a black or gray body thermal emitter.

7. The apparatus of claim 6 wherein the source is amplitude modulated by a mechanical chopping system in order to increase a signal to noise ratio of a subsequently received electromagnetic signal.

8. The apparatus of claim 5 wherein the source comprises a semiconductor LED type emitter or array of emitters.

9. The apparatus of claim 8 wherein the source is pulsed in order to increase a signal to noise ratio of a subsequently received electromagnetic signal.

10. The apparatus of claim 1 wherein the sensor device is comprised of a one or two-dimensional array of photosensitive elements.

11. The apparatus of claim 10 further comprising a processor which receives the output of the sensor device and operates on the output to determine the state, quality, or acceptability of the objects.

12. The apparatus of claim 11 further comprising part detection, tracking, and conveyance systems deployed to interact with the objects and used to both maneuver the object under test into an advantageous position between the sensor device and source and to provide instrument control signals to both the sensor device and source.

13. The apparatus of claim 12 further comprising a reject system which receives the processed output of the processor and acts to physically reject or otherwise mark for subsequent action objects.

14. The apparatus of claim 13 wherein the source comprises a black or gray body thermal emitter.

15. The apparatus of claim 14 wherein the source is amplitude modulated by a mechanical chopping system in order to increase a signal to noise ratio of a subsequently received electromagnetic signal.

16. The apparatus of claim 15 wherein the source comprises a semiconductor LED type emitter or array of emitters.

17. The apparatus of claim 16 wherein the source is pulsed in order to increase a signal to noise ratio of a subsequently received electromagnetic signal.

18. A sensing method wherein visibly clear objects are inspected for structural integrity, the method comprising steps of:
   placing a visibly clear object under test disposed in between a sensor device and a source of electromagnetic radiation;
   generating electromagnetic radiation in wavelength ranges such that the objects are substantially opaque due to naturally occurring molecular or atomic absorptions occurring in material comprising the objects, the ranges corresponding to both the opaque wavelength regions of the objects and sensitivity regions of the sensing device;
   sensing with the sensor device the electromagnetic radiation at the wavelengths which correspond to the opaque wavelength regions of the objects under test; and,
   determining a state, quality, or acceptability of the objects based on an output of the sensor device.

19. The method of claim 18 wherein the sensing comprises using a single-element photoconductive, photovoltaic, or thermal detector.

20. The method of claim 19 further comprising using processing means to receive output of the sensor device and to operate on the output to deter mine a state, quality, or acceptability of the objects.

21. The method of claim 20 further comprising using part detection, tracking, and conveyance systems deployed to interact with the objects and useful to both maneuver the objects into an advantageous position between the sensor device and a source of the electromagnetic radiation and to provide instrument control signals to both the sensor device and the source.

22. The method of claim 21 further comprising using a reject system to receive processed output of the processing means and to physically reject or otherwise mark objects.

23. The method of claim 22 wherein the generating comprising using a black or gray body thermal emitter.

24. The method of claim 23 wherein the generating comprises amplitude modulating the radiation by a mechanical chopping system in order to increase a signal to noise ratio of a subsequently received electromagnetic signal.

25. The method of claim 22 wherein the generating comprises using a semiconductor LED type emitter or array of emitters.

26. The method of claim 25 further comprising pulsing the source in order to increase a signal to noise ratio of a subsequently received electromagnetic signal.

27. The method of claim 18 wherein the sensing comprising using a one or two-dimensional array of photosensitive elements.

28. The method of claim 27 further comprising using processing means to receive the output of the sensor device and to operate on the output to determine a state, quality, or acceptability of the objects.

29. The method of claim 28 further comprising using part detection, tracking, and conveyance means deployed to interact with the objects and useful to both maneuver the objects into an advantageous position between the sensor device and a source of electromagnetic radiation and to provide instrument control signals to both the sensor device and the source.

30. The method of claim 29 further comprising using a reject system to receive processed output of the processing means and to physically reject or otherwise mark objects.

31. The method of claim 30 wherein the generating comprises using a black or gray body thermal emitter.

32. The method of claim 31 wherein the generating comprises using a mechanical chopping system to amplitude modulate in order to increase a signal to noise ratio of a subsequently received electromagnetic signal.

33. The method of claim 32 wherein the generating comprises using a semiconductor LED type emitter or array of emitters.

34. The method of claim 33 wherein the generating comprises pulsing to increase a signal to noise ratio of a subsequently received electromagnetic signal.

* * * * *